United States Patent [19]
Kwon et al.

[11] Patent Number: 5,942,511
[45] Date of Patent: Aug. 24, 1999

[54] ALLYLTHIOPYRIDAZINE DERIVATIVES AND PROCESS FOR PREPARING THE SAME

[75] Inventors: Soon Kyoung Kwon; Sang Geon Kim; Young Nam Park; Mi Kyung Kim; Sung Hee Choi; Hea Soon Shin, all of Seoul, Rep. of Korea

[73] Assignees: Soon Kyoung Kwon, Seoul; Seoul Pharm. Co., Ltd., Kyunggi-do, both of Rep. of Korea

[21] Appl. No.: 09/098,275

[22] Filed: Jun. 16, 1998

[30] Foreign Application Priority Data

Jan. 16, 1998 [KR] Rep. of Korea ................. 98-1153

[51] Int. Cl.$^6$ ................. A61K 31/50; C07D 237/30; C07D 237/32; C07D 237/18
[52] U.S. Cl. ................. 514/247; 544/224; 544/239; 544/240; 544/241; 544/237; 514/248
[58] Field of Search ................. 544/237, 239, 544/240, 241; 514/247, 248

[56] References Cited

U.S. PATENT DOCUMENTS 4,136,176 1/1979 Maurer et al. ................. 424/200
5,550,134 8/1996 Audia et al. ................. 514/284

*Primary Examiner*—Emily Bernhardt
*Attorney, Agent, or Firm*—Ladas & Parry

[57] ABSTRACT

The, present invention relates to a novel allylthiopyridazine derivative represented by formula (I) which exhibits a superior effect for prevention and treatment or hepatic diseases induced by toxic substances and for protection of human tissues from radiation:

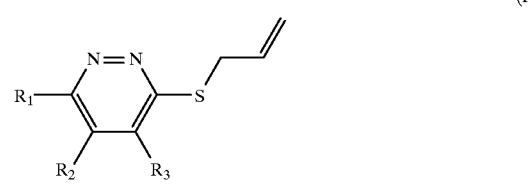

(I)

or a pharmaceutically acceptable salt thereof, in which $R_1$ represents halogen atom, lower alkoxy, dialkylaminoalkoxy, hydroxyalkoxy, phenoxy substituted or unsubstituted with lower alkyl, benzyloxy, or phenyl, and $R_2$ and $R_3$ independently of one another represent hydrogen or lower alkyl, or $R_2$ and $R_3$ together with carbon atom to which they are attached can form a saturated or unsaturated 6-membered ring, provided that $R_2$ and $R_3$ are other than hydrogen when $R_1$ is chloro; and to a process for preparing thereof and a pharmaceutical composition containing the same as an effective component.

12 Claims, 3 Drawing Sheets

ALLYLTHIOPYRIDAZINE DERIVATIVES AND PROCESS FOR PREPARING THE SAME

TECHNICAL FIELD

The present invention relates to a novel allylthiopyridazine derivative represented by formula (I), which exhibits a superior effect for prevention and treatment of hepatic diseases induced by toxic substances and for protection of human tissues from radiation:

or a pharmaceutically acceptable salt thereof, in which
  $R_1$ represents halogen atom, lower alkoxy, dialkylaminoalkoxy, hydroxyalkoxy, phenoxy substituted or unsubstituted with lower alkyl, benzyloxy, or phenyl, and
  $R_2$ and $R_3$ independently of one another represent hydrogen or lower alkyl, or $R_2$ and $R_3$ together with carbon atom to which they are attached can form a saturated or unsaturated 6-membered ring,
provided that $R_2$ and $R_3$ are other than hydrogen when $R_1$ is chloro.

In addition, the present invention relates to a process for preparing the compound of formula (I) as above, a novel intermediate used in this process, and a pharmaceutical composition containing the compound of formula (I) as an effective component.

BACKGROUND ART

Oltipraz increases the expression rate of microsomal epoxide hydrolase (mEH) and glutathione S-transferases (GST), intracellular oxidoreductases, thus increasing their levels in cells. Oltipraz has been known to protect the cellular tissue from radiation [see, S. G. Kim, et al., *Molecular Pharmacology*, 51, 225–233, 1997; S. Y. Nam, et al., *Radiation Research*, 147, 613–620, 1997]. That is, it can be noted that the increase in intracellular expression rate of mEH and GST is closely related to the protection of cells from radiation. Further, it has been generally recognized that the increase in intracellular expression rate of mEH and GST is also related to the protection of human body from toxic substances [see, Ansher et al., *Hepatology*, 3, 932–935, 1983; Lu & Miwa, *Annual Review of Pharmacology and Toxicology*, 20, 513–531, 1980].

It has been reported that the tissue damage induced by toxic substances such as acetaminophen or carbon tetrachloride has a close relation with the activity of cytochrome P450 2E1 which metabolizes such toxic substances [see, S. K. Kim, et al., *J Pharmacol. Exp. Therap.* 277, 1058, 1996]. Thus, when laboratory rats are treated with a pyridine, a cytochrome P450 2E1 derivative, serious hepatic damage occurs even at low concentration of carbon tatrachloride. Therefore, it has been anticipated that if the activity of cytochrome P450 2E1 can be effectively inhibited, the tissue damage to human organs (particularly, liver) due to toxic substances may be avoided and, for the same reason, human body may also be protected from oncogenic substances, radiation, antitumor chemotherapeutics, etc, to small intestine, colon, gall bladder, bronchus, pancreas, mammary gland and skin.

As one of the therapeutic agents, which are presently used in the clinical field for the prevention and treatment of hepatic diseases induced by toxic substances, malotilate has been shown to have a good effect of preventing and treating hepatic diseases induced by carbon tetrachloride and acetaminophen. In addition, it has been also recognized that diallyl sulfide and allicin as one of aromatic substances in garlic oil have the effect of inhibiting oncogenesis due to 1,2-dimethylhydrazine and protecting liver from hepatotoxicity of 1,2-dimethylhydrazine.

Given much technical knowledge in the conventional art, the present inventors have considered the possibility that the allylthio group may play an important role in protecting human organs from toxic substances or radiation, and by increasing the intracellular expression of mEH and GST, at the same time, effectively inhibits the activity of cytochrome P450 2E1 as mentioned above. Thus, we have extensively conducted a study to newly synthesize numerous compounds having allylthio group and to examine their pharmacological activities. As a result, we have identified that the compound of formula (I), as defined above, in which allylthio group as a pharmacologically active group is introduced into pyridazine nucleus and a substituent such as halogen, alkoxy, etc., is introduced into the para-position of allylthio group, can protect human tissues from radiation and active toxic substances by increasing the expression of mEH and GST, and at the same time, by inhibiting the expression of metabolic enzymes.

DISCLOSURE OF THE INVENTION

Accordingly, the present invention relates to a novel allylthiopyridazine derivative of formula (I), as defined above, and a pharmaceutically acceptable salt thereof.

Further, the present invention relates to a novel process for preparing the compound of formula (I).

In addition, the present invention relates to a pharmaceutical composition for prevention and treatment of hepatic diseases, which comprises as an effective component the compound of formula (I) or its salt together with a pharmceutically acceptable carrier.

Also, the present invention relates to a pharmaceutical composition for protection of human tissues from radiation, which comprises as an effective component the compound of formula (I) or its salt together with a pharamceutically acceptable carrier.

BRIEF DESCRIPTION OF DRAWINGS

For a thorough understanding of the nature and objects of the present invention, reference should be made to the following detailed description taken in connection with the accompanying drawings in which.

BEST MODE FOR CARRYING OUT THE INVENTION

Hereinafter, the present invention will be more specifically explained.

The present invention relates to a novel allylthiopyridazine derivative represented by formula (I), which exhibits a superior effect for prevention and treatment of hepatic diseases induced by toxic substances and for protection of human tissues from radiation:

(I)

or a pharmaceutically acceptable salt thereof, in which
  $R_1$ represents halogen atom, lower alkoxy, dialkylaminoalkoxy, hydroxyalkoxy, phenoxy substituted or unsubstituted with lower alkyl, benzyloxy, or phenyl, and
  $R_2$ and $R_3$ independently of one another represent hydrogen or lower alkyl, or $R_2$ and $R_3$ together with carbon atom to which they are attached can form a saturated or unsaturated 6-membered ring,
provided that $R_2$ and $R_3$ are other than hydrogen when $R_1$ is chloro.

Among the compounds of formula (I) having a superior pharmacological effect, the preferred compounds include those wherein $R_1$ represents chloro, methoxy, ethoxy, n-propoxy, 2-propoxy, n-butoxy, 2-butoxy, t-butoxy, n-pentyloxy, i-pentyloxy, 2-(N,N-dimethylamino)ethoxy, 2-hydroxyethoxy, phenoxy, benzyloxy, 4-methylphenoxy, 3-methylphenoxy, 2-methylphenoxy or phenyl, and $R_2$ and $R_3$ independently of one another represent hydrogen or methyl, or $R_2$ and $R_3$ together with carbon atom to which they are attached forms a saturated or unsaturated 6-membered ring.

The pharmaceutically acceptable salts of the compound of formula (I) according to the present invention may include pharmaceutically acceptable acid addition salts such as asparaginate, gluconate, glutamate, hydrochloride, p-toluenesulfonate or citrate, salts with alkaline metal such as sodium, potassium or lithium, or salts with other acid or base which has been known to be conventionally used for compounds such as diallyl sulfide, allicin, etc. These salts can be readily prepared by conventional transformation method from the free compound of formula (I).

In addition, the compound of formula (I) according to the present invention can be prepared by a process characterized in that (a) a compound of formula (II):

(II)

wherein $R_1$, $R_2$ and $R_3$ are defined as above and X represents a reactive leaving group, is reacted with a compound of formula (III):

$$HS-CH_2-CH=CH_2 \quad (III)$$

in a solvent in the presence of a base to produce the compound of formula (I); or (b) a compound of formula (IV):

(IV)

wherein X represents a reactive leaving group, is reacted with a compound of formula (V):

$$R_1'ONa \quad (V)$$

wherein $R_1'$ represents lower alkyl, dialkylaminoalkyl, hydroxyalkyl, phenyl substituted or unsubstituted with lower alkyl, or benzyl, in a solvent to produce a compound of formula (Ia):

(Ia)

wherein $R_1'$ is defined as above.

Accordingly, another purpose of the present invention is to provide such a process for preparing the compound of formula (I).

In the variant (a), one or more selected from the group consisting of methanol, ethanol, acetone and methylethyl ketone can be used as the solvent; and one or more selected from the group consisting of alkaline metals such as sodium, potassium, lithium, etc. can be used as the base. Preferably, the reaction is conducted for 1 to 24 hours under reflux with heating.

The solvent which can be used in the variant (b) may be the same as those mentioned in the variant (a) above. The compound of formula (V) used as the reactant in this method is prepared by reacting sodium with a compound of formula $R_1'OH$ in the reaction vessel and then immediately used for reaction with the compound of formula (IV). The reaction is conducted for 24 hours under reflux with heating.

Meanwhile, the compound of formula (II) used as the starting material in the variant (a) is a novel compound. Therefore, still another purpose of the present invention is to provide the novel compound of formula (II) as defined above.

The compound of formula (II) can be prepared by a process shown in the following reaction schemes 1 and 2. The specific method can be seen in Preparation examples described below.

Reaction scheme 1

In the above reaction scheme, $R_1$, $R_2$, $R_3$ and X are defined as above.

In the above reaction scheme 1, the compound of formula $R_1$—H added to the reaction solution is reacted with an alkaline metal to form the alkaline metal salt, and the resulting alkaline metal salt is reacted with the starting material to produce the compound of formula (II). This reaction is generally conducted at room temperature or under warming. The reaction can be completed within 30 minutes to 12 hours.

Alternatively, the compound of formula (II) wherein the reactive leaving group is chloro and the $R_1$ position is also substituted with chloro can be prepared by reacting the compound wherein both the 3- and 6-positions of pyridazine ring are substituted with hydroxy with phosphorus oxychloride ($POCl_3$), as shown in the following reaction scheme 2. In this method, the reaction is conducted for 5 to 10 hours under reflux with heating.

Reaction scheme 2

In the above reaction scheme, $R_2$ and $R_3$ are defined as above.

The compound of formula (IV) (X=Cl) used as the starting material in the reaction variant (b) for preparing the compound of formula (I) is a known compound and can be prepared by referring to the method disclosed in literature [see, M. Kocevar et al., Croat. Chem. Acta., 45, 457, 1973].

Figure 1:
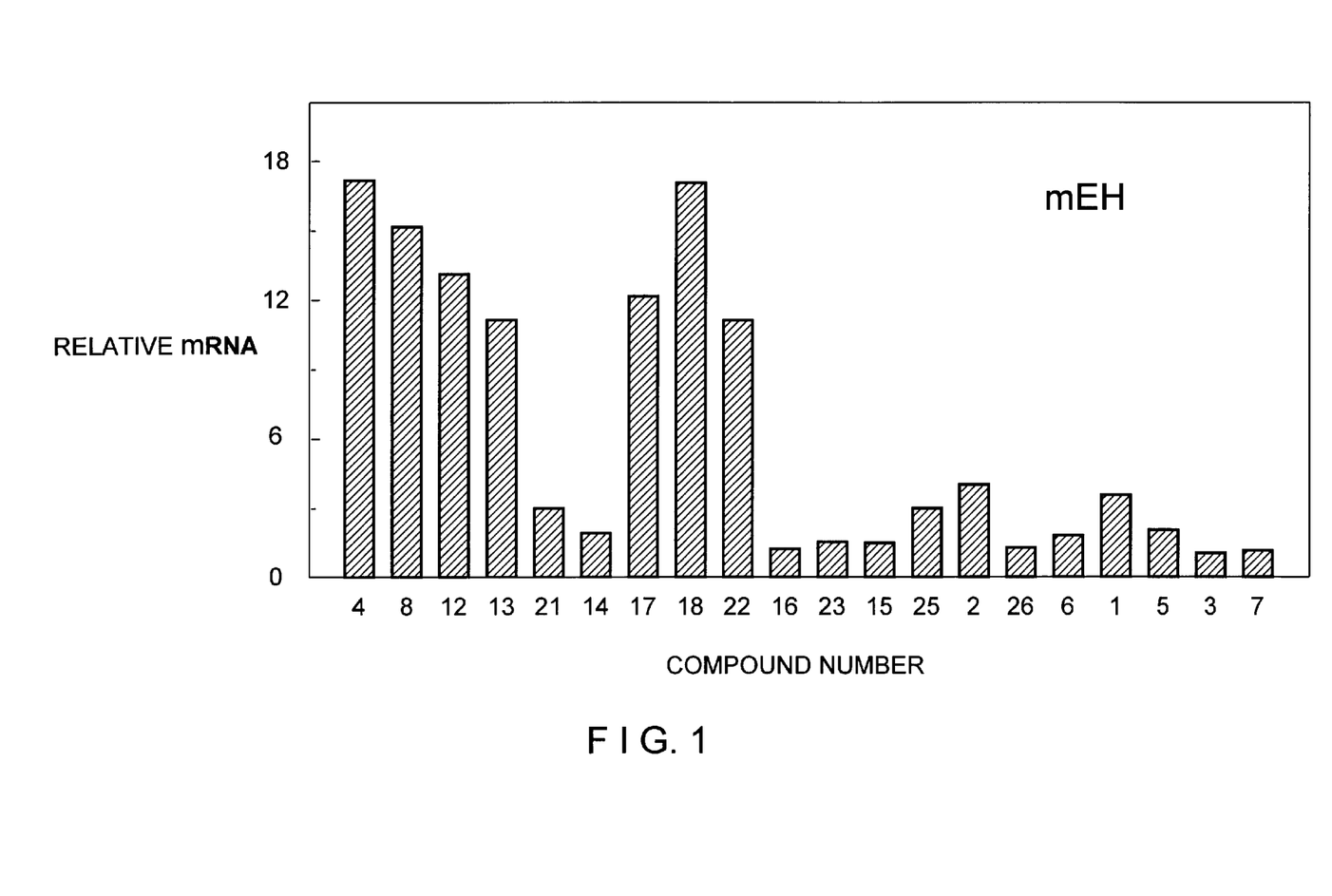
FIG. 1 shows the result of Northern Blot analysis for measuring an increase in mRNA of microsomal epoxide hydrolase in liver tissue 24 hours after administration of the compound according to the present invention.
Figure 2:
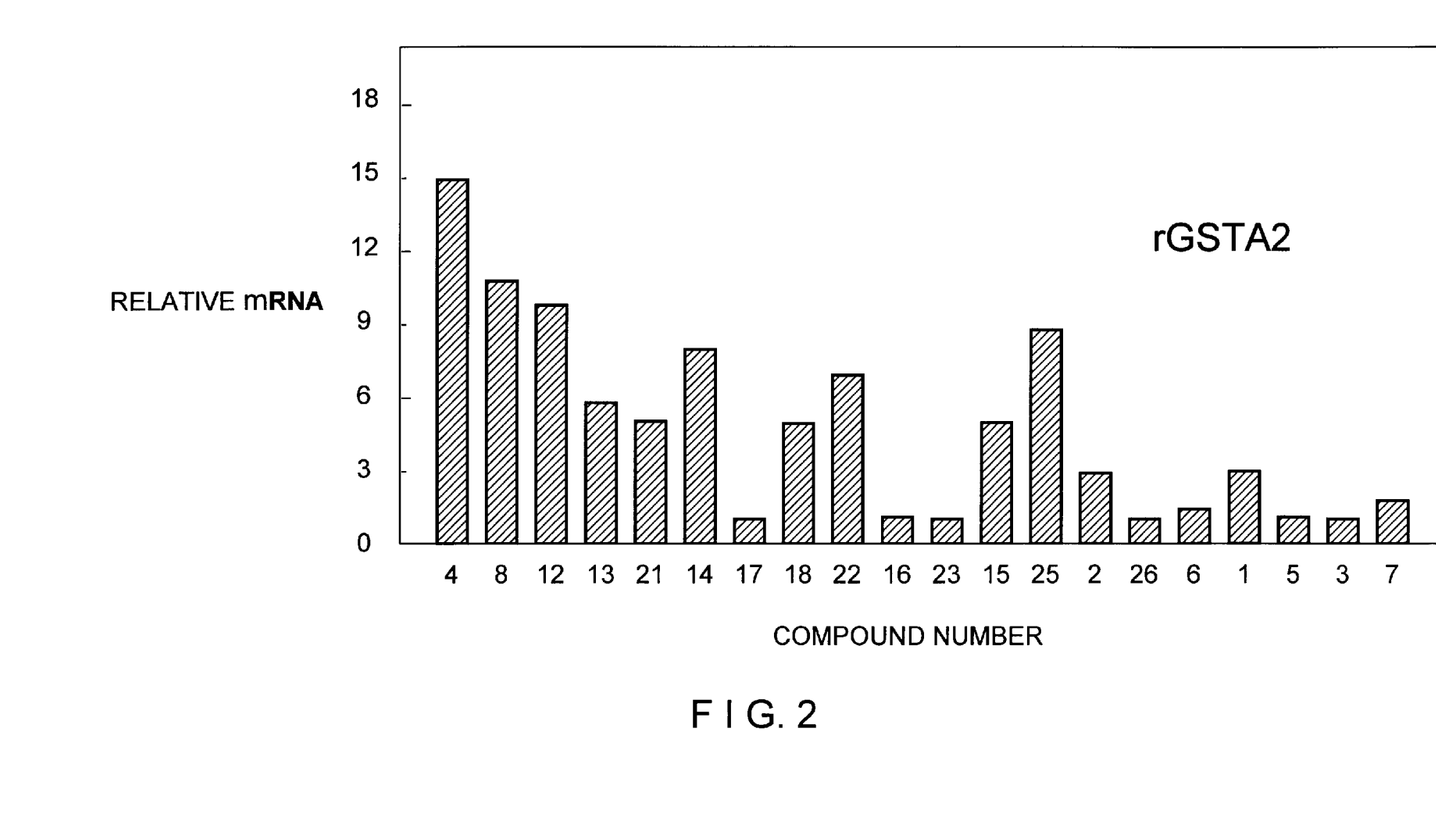
FIG. 2 shows the result of Northern Blot analysis for measuring an increase in mRNA of glutathione S-transferases A2 in liver tissue 24 hours after administration of the compound according to the present invention.

In order to confirm the effect of allylthiopyridazine derivatives according to the present invention on the expression rate of mEH and GST, the present inventors have quantified the amount of mRNAs of mEH and GSTA2 produced in liver tissue after a certain period from the oral administration of the respective compound to mouse, according to Northern Blot analysis (see FIGS. 1 and 2). As a result, we could observe a significant increase in the expression rate of mRNA. Such mRNA increasing effect of the compound of formula (I) is considered as having the direct relationship with the effect for prevention and treatment of hepatic diseases induced by toxic substances and protection of human tissues from radiation. Therefore, the present inventors have conducted the following experiment to determine the effects of the compound of formula (I) for prevention and treatment of hepatic diseases and protection of human tissues from radiation.

First, the effects of allylthiopyridazine derivative of formula (I) for prevention and treatment of hepatic diseases was examined using carbon tetrachloride model and acetaminophen model.

Carbon tetrachloride model [see, Philippe letteron et al., Biochemical Pharmacology, 39, 12, 2027–2034, 1990] is most frequently used as an experimental model of hepatic disorder and has been established on the basis of the fact that carbon tetrachloride is converted into trichloromethyl free radical ($CCl_3$ .), a highly toxic metabolite, by the action of cytochrome P-450 in body. This metabolite strongly binds with thiol group of liver microsomal membrane protein to produce a lipid radical, which is then converted into peroxy radical in the presence of oxygen, thereby stimulating the peroxidation reaction of membrane lipid. That is, carbon tetrachloride inhibits protein biosynthesis in liver, increases blood ALT (alanine aminotransferase) and causes centrilobular necrosis of liver cells.

In addition, the liver protective effects of the compound of the present invention can also be confirmed by acetaminophen model [see, Wang et al., Toxicology and applied Pharmacology, 136, 146–154, 1996]. Acetaminophen is rapidly metabolized by CYP2E1 to cause hepatic toxicity, which results in structural and functional change in liver cellular membrane, causing necrosis in hepatic lobule, an increase in blood ALT and LDH (lactate dehydrogenase) levels.

In the present invention, the inhibiting effect of the compound of formula (I) on hepatic disorder, induced by carbon tetrachloride and acetaminophene, was determined after oral administration of the novel compound according to the present invention to mouse as the experimental animal for 3 days. The degree of liver damage in respective experimental animal was determined by measuring ALT and LDH levels in blood [see, Biol. Pharm. Bull., 20, 4, 381–385, 1997; Toxicology and Applied Pharmacology, 95, 1–11, 1988], and further by removing the liver, staining (×100) the liver with hematoxylin and eosin and then observing with microscope to examine the degree of hepatocyte necrosis. As a result of this experiment, it has been identified that the compound of formula (I) according to the present invention has a superior liver protective effect even in comparison to silymarin which has been broadly known as liver protective agent.

Further, the present inventors have confirmed the protective effect of allylthiopyridazine derivative according to the present invention against radiation by administering the active compound to mouse, irradiating the radiation of 8 or 9Gy and, after a certain period, measuring the survival rate of mouse. For example, the survival rate during 30 days of 8Gy radiation can be seen from FIG. 3, and the specific experimental result is described in the following Table 7. Specifically, when 8Gy radiation is used, the survival rate during 30 days in the groups which only radiation was used was merely 48%, whereas the survival rates during 30 days in the groups to which the compounds of Examples 4 and 8 are previously administered were 76% and 70%, respectively. Therefore, it can be noted that the protective effect of the compound according to the present invention against radiation is proven to be a very significant novel discovery.

Moreover, as a result of an acute toxicity test using mouse to evaluate the general toxicity of the compound according to the present invention, when the compound is single administered via oral route, the $LD_{50}$ value of the respective compound is 3.5 g/kg or more. Therefore, the compound of the present invention is determined as being very safe.

From the above experimental results, it can be identified that the compound of formula (I) according to the present invention is safe and has an excellent effect of preventing and treating hepatic diseases. Therefore, further purpose of the present invention is to provide a pharmaceutical composition for prevention and treatment of hepatic diseases, which comprises as an effective component the compound of formula (I) or its pharmaceutically acceptable salt. In addition, since the compound of the present invention and its salt are identified as having a protective effect against radiation, the composition for protection of human tissues from radiation, which comprises the said compound as an effective component, is also a subject of the present invention. Such effects of the pharmaceutical composition according to the present invention are related to the acting mechanism of the compound of formula (I), which increases the expression rate of mEH and GST as oxidoreductases and also inhibits the activity of cytochrome P450 2E1. As mentioned above, since the acting mechanism, which increases the expression rate of mEH and GST and inhibits the activity of cytochrome P450 2E1, is related to the effects of reducing the toxicity of antitumor chemotherapeutics and inhibiting oncogenesis due to chemical substances, as well as the effects of preventing and treating hepatic disease and protecting human tissues from radiation, it could be understood that the compound of the present invention may also exhibit such effects.

When using the pharmaceutical composition according to the present invention for a clinical purpose, the compound of formula (I) can be formulated in combination with a pharmaceutically acceptable inert carrier into a solid, semi-solid or liquid pharmaceutical preparation suitable for oral or parenteral administration.

Pharmaceutically acceptable inert carrier which can be used for this purpose may be solid or liquid and include one or more selected from a group consisting of diluent, flavoring agent, solubilizing agent, lubricant, suspending agent, binder, tablet swelling agent, etc. As a specific example of the suitable solid or liquid carrier which can be used in the present invention, starch, lactose, cellulose derivatives (Avicel®), sugar, etc. may be mentioned.

When using the pharmaceutical composition according to the present invention for the purpose of preventing and treating hepatic diseases and protecting liver from radiation, the daily dosage of the active compound according to the present invention is preferably 1 to 500 mg per kg of body weight, at the initial stage. However, it should be understood that the dosage can be varied depending on the needs of the patients, the severity of disease to be treated, the kind of the compound used, etc. and the optimum dosage can be determined according to the known method by a person skilled in this art. In general, the therapeutic procedure is initiated at a dosage level which is lower than the optimum dosage of the compound and then gradually increasing the dosage depending on the condition until the optimum effect is obtained. If appropriate, the total daily dosage may be divided into some portions and then administered over one day period.

The present invention is more specifically explained by the following preparations and examples. However, it should be understood that these preparations and examples are only intended to assist the understanding of the present invention but the present invention is not limited to these examples in any manner.

Preparation 1
Synthesis of 3,6-dihydroxy-4,5-dimethylpyridazine 50 ml of purified water was added to 3.4 ml(0.07 mol) of hydrazine monohydrate and then 14 ml(0.14 mol) of conc. hydrochloric acid was added dropwise thereto. Then, the reaction solution was warmed to boil. When the reaction mixture begins to reflux, 8.83 g(0.07 mol) of 2,3-dimethylmaleic acid anhydride was added thereto. The reaction solution was continuously refluxed for 3 hours and then cooled. The precipitated white crystal was filtered, washed with purified water, dissolved in boiling purified water to remove insoluble material and then recrystallized to obtain the title compound as an amorphous white crystal.

Yield: 9.10 g (92.8%)

Melting Point: 298–300° C. (decomposition)

Recrystallizing solvent: water

NMR(CDCl$_3$+DMSO-d$_6$, δ): 2.00(s, 3H×2, CH$_3$), 3.30(s, 1H×2, OH)

Preparation 2
Synthesis of 1,4-dihydroxy-5,6,7,8-tetrahydrophthalazine 25 ml of purified water was added to 1.7 ml(0.035 mol) of hydrazine monohydrate and then 7 ml(0.07 mol) of conc. hydrochloric acid was added dropwise thereto. Then, the reaction solution was warmed to boil. When the reaction mixture begins to reflux, 5.33 g(0.035 mol) of 3,4,5,6-tetrahydrophthalic acid anhydride was added thereto. The reaction solution was continuously refluxed for 3 hours and then cooled. Then, the reaction solution was treated according to the same manner as Preparation 1 to obtain the title compound as an white needle crystal.

Yield: 5.47 g (94.0%)

Melting Point: 298–300° C., (decomposition)

Recrystallizing solvent: water

NMR(CDCl$_3$+DMSO-d$_6$, δ): 1.65(s, 2H×2, CH$_2$), 2.35(s, 2H×2, CH$_2$), 3.30(s, 1H×2, OH)

Preparation 3
Synthesis of 3,6-dichloro-4,5-dimethylpyridazine 2.80 g(0.02 mol) of completely dried 3,6-dihydroxy-4,5-dimethylpyridazine (obtained from Preparation 1) was added to 20 ml of phosphorus oxychloride (POCl$_3$), and the reaction mixture was refluxed for 7 hours. At this time, the point when the colorless reaction solution is changed into purple was considered as the end point of the reaction. The reaction solution was concentrated under reduced pressure to remove excessive phosphorus oxychloride. The small quantity of ice water was added to the residue and then stirred to form a suspension. Until the suspension becomes alkaline, 28% aqueous ammonium hydroxide solution was added to the suspension to produce brown precipitate. The precipitate was filtered and then dissolved in hot ethanol to remove insoluble material. Active carbon was added to the resulting solution and the mixture was refluxed for 5 minutes, decolorized by passing through silicon dioxide and then distilled under reduced pressure to remove excessive ethanol. In this manner, the title compound was obtained as a white needle crystal.

Yield: 2.45 g (69.2%)

Melting Point: 109–111° C.

Recrystallizing solvent: ethanol

NMR(CDCl$_3$, δ): 2.05(s, 3H×2, CH$_3$)

Preparation 4
Synthesis of 1,4-dichloro-5,6,7,8-tetrahydrophthalazine 3.32 g(0.02 mol) of completely dried 1,4-dihydroxy-5,6,7,8-tetrahydrophthalazine (obtained from Preparation 2) was added to 20 ml of phosphorus oxychloride. Then, the reaction was carried out according to the same manner as Preparation 3 to obtain the title compound as a white needle crystal.

Yield: 2.68 g (66.0%)

Melting Point: 148–150° C.

Recrystallizing solvent: ethanol

NMR(CDCl$_3$, δ): 1.85(s, 2H×2, CH$_2$), 2.75(s, 2H×2, CH$_2$)

Preparation 5
Synthesis of 3-methoxy-4,5-dimethyl-6-chloropyridazine 0.46 g(0.02 mol) of metallic sodium was dissolved in 30 ml of absolute methanol and then 3.54 g(0.02 mol) of 3,6-dichloro-4,5-dimethylpyridazine obtained from Preparation 3 was added thereto and completely dissolved. The reaction solution was stirred for one hour at room temperature and concentrated under reduced pressure to remove excessive methanol. 100 ml of diethyl ether was added to the residue and then vigorously stirred for 10 minutes. The diethyl ether-insoluble materials were removed off and the remaining solution was washed two times with 50 ml of purified water, dried over anhydrous sodium sulfate and then concentrated under reduced pressure to remove diethyl ether. In this manner, the title compound was obtained as a white needle crystal.

Yield: 2.63 g (76.2%)

Melting Point: 80–82° C.

Recrystallizing solvent: ethanol

Preparation 6
Synthesis of 1-methoxy-4-chloro-5,6,7,8-tetrahydrophthalazine 0.34 g(0.015 mol) of metallic sodium was dissolved in 30 ml of absolute methanol and then 3.05 g(0.015 mol) of 1,4-dichloro-5,6,7,8-tetrahydrophthalazine obtained from Preparation 4 was added thereto and completely dissolved. The reaction solution was stirred for one hour at room temperature, and then treated according to the same manner as Preparation 5 to obtain the title compound as a white needle crystal.

Yield: 1.78 g (59.7%)

Melting Point: 117–119° C.

Recrystallizing solvent: ethanol

Preparation 7
Synthesis of 1-methoxy-4-chlorophthalazine 0.23 g(0.01 mol) of metallic sodium was dissolved in 50 ml of absolute methanol and then 1.99 g(0.01 mol) of 1,4-dichlorophthalazine was added thereto and completely dissolved. The reaction solution was stirred for one hour at room temperature and then treated according to the same manner as Preparation 5 to obtain the title compound as an amorphous white crystal.

Yield 1.81 g (92.8%)

Melting Point: 92–94° C.

Recrystallizing solvent: ethanol

NMR(CDCl$_3$, $\delta$): 4.28(s, 3H, OCH$_3$), 7.90–8.25(m, 1H×4, aromatic)

Preparation 8
Synthesis of 3-ethoxy-4,5-dimethyl-6-chloropyridazine 0.69 g(0.03 mol) of metallic sodium was dissolved in 100 ml of absolute ethanol and then 5.31 g(0.03 mol) of 3,6-dichloro-4,5-dimethylpyridazine was added thereto and completely dissolved. The reaction solution was stirred for 4 hours at room temperature and then treated according to the same manner as Preparation 5 to obtain the title compound as a pale white crystal.

Yield: 4.22 g (75.4%)

Melting Point: 60–62° C.

Recrystallizing solvent: ethanol

NMR(CDCl$_3$, $\delta$): 1.42(t, 3H, CH$_3$), 2.20((s, 3H, CH$_3$), 2.32(s, 3H, CH$_3$), 4.52(q, 2H, OCH$_2$)

Preparation 9
Synthesis of 1-ethoxy-4-chloro-5,6,7,8-tetrahydrophthalazine 0.69 g(0.03 mol) of metallic sodium was dissolved in 100 ml of absolute ethanol and then 6.09 g(0.03 mol) of 1,4-dichloro-5,6,7,8-tetrahydrophthalazine obtained from Preparation 4 was added thereto and completely dissolved. The reaction solution was stirred for 4 hours at room temperature and then treated according to the same manner as Preparation 5 to obtain the title compound as a pale white crystal.

Yield: 5.98 g (93.7%)

Melting Point: 105–107 20 C. P1 Recrystallizing solvent: ethanol

NMR(CDCl$_3$, $\delta$): 1.40(t, 3H, CH$_3$), 1.80–2.65(m, 2H×4, aromatic), 4.52(q, 2H, OCH$_2$)

Preparation 10
Synthesis of 1-ethoxy-4-chlorophthalazine 0.69 g(0.03 mol) of metallic sodium was dissolved in 100 ml of absolute ethanol and then 5.97 g(0.03 mol) of 1,4-dichlorophthalazine was added thereto and completely dissolved. The reaction solution was stirred for one hour at 50±10° C. and then treated according to the same manner as Preparation 5 to obtain the title compound as a white needle crystal.

Yield: 5.02 g (80.2%)

Melting Point: 76–78° C.

Recrystallizing solvent: ethanol

NMR(CDCl$_3$, $\delta$): 1.55(t, 3H, CH$_3$), 4.70(q, 2H, OCH$_2$), 7.92–8.20(m, 1H×4, aromatic)

EXAMPLE 1
Synthesis of 3-chloro-4,5-dimethyl-6-allylthiopyridazine 0.23 g(0.01 mol) of metallic sodium was dissolved in 40 ml of absolute methanol and the resulting solution was mixed with 0.93 ml (0.01 mol) of allylmercaptan (CH$_2$=CH—CH$_2$—SH). To this mixture, 1.77 g(0.01 mol) of 3,6-dichloro-4,5-dimethylpyridazine obtained from Preparation 3 was added, and the reaction solution was refluxed for one hour and then concentrated under reduced pressure to remove methanol. 50 ml of diethyl ether was added to the residue and vigorously stirred for 10 minutes. Diethyl ether-insoluble materials were removed off and the remaining solution was washed two times with 30 ml of purified water, dried over anhydrous sodium sulfate and concentrated under reduced pressure to obtain the residue as a yellow oil. The obtained residue was subjected to TLC to obtain 5 spots (Rf=0.8, 0.6, 0.5, 0.2, 0.1). Among them, the title compound having Rf value 0.5 was separated by silica gel column chromatography (eluent: n-hexane/ethyl acetate=5/1, v/v). The eluent was removed under reduced pressure and the residue was concentrated to obtain a white oil, which was dried for 2 hours under high vacuum to obtain the title compound as a freezing white crystal.

Yield: 1.16 g (54.0%)

Melting Point: 51–53° C.

NMR(CDCl$_3$, $\delta$): 2.25(s, 3H, CH$_3$), 2.35(s, 3H, CH$_3$), 3.95(d, 2H, SCH$_2$), 5.25(dd, 2H, CH$_2$), 6.00(m, 1H, CH)

EXAMPLE 2
Synthesis of 1-chloro-4-allylthio-5,6,7,8-tetrahydrophthalazine 0.23 g(0.01 mol) of metallic sodium was dissolved in 30 ml of absolute methanol and then mixed with 0.93 ml(0.01 mol) of allylmercaptan. To this mixture was added 2.03 g(0.01 mol) of 1,4-dichloro-5,6,7,8-tetrahydrophthalazine obtained from Preparation 4. The reaction solution was refluxed for one hour and then treated according to the same manner as Example 1 to obtain the title compound as a freezing white crystal.

Yield: 1.81 g (75.1%)

Melting Point: 43–45° C.

NMR(CDCl$_3$, δ): 1.85–2.65(m, 2H×4, aromatic), 3.95(d, 2H, SCH$_2$), 5.25(dd, 2H, CH$_2$), 6.00(m, 1H, CH)

EXAMPLE 3
Synthesis of 1-chloro-4-allylthiophthalazine 0.23 g(0.01 mol) of metallic sodium was dissolved in 30 ml of absolute methanol and then mixed with 0.93 ml (0.01 mol) of allylmercaptan. To this mixture was added 1.99 g(0.01 mol) of 1,4-dichlorophthalazine. The reaction solution was refluxed for 24 hours and then treated according to the same manner as Example 1 to obtain the title compound as a pale white needle crystal.

Yield: 1.27 g (53.6%)

Melting Point: 76–78° C.

NMR(CDCl$_3$, δ): 4.15(d, 2H, SCH$_2$), 5.30(dd, 2H, CH$_2$), 6.10(m, 1H, CH), 8.10(m, 1H×4, aromatic)

EXAMPLE 4
Synthesis of 3-methoxy-6-allylthiopyridazine 1.15 g(0.05 mol) of metallic sodium was dissolved in 50 ml of absolute methanol and then mixed with 4.98 ml(0.05 mol) of allylmercaptan. To this mixture was added 7.23 g(0.05 mol) of 3-methoxy-6-chloropyridazine. The reaction solution was refluxed for 24 hours and then treated according to the same manner as Example 1 to obtain the title compound as a freezing pale white crystal.

Yield: 3.99 g (53.7%)

Melting Point: 25–27° C.

NMR(CDCl$_3$, δ): 3.95(d, 2H, SCH$_2$), 4.08(s, 3H, OCH$_3$), 5.25(dd, 2H, CH$_2$), 6.00(m, 1H, CH), 6.80–7.30(dd, 1H×2, CH)

EXAMPLE 5
Synthesis of 3-methoxy-4,5-dimethyl-6-allylthiopyridazine 0.23 g(0.01 mol) of metallic sodium was dissolved in 30 ml of absolute methanol and then mixed with 0.93 ml(0.01 mol) of allylmercaptan. To this mixture was added 1.73 g(0.01 mol) of 3-methoxy-4,5-dimethyl-6-chloropyridazine obtained from Preparation 5. The reaction solution was refluxed for one hour and then treated according to the same manner as Example 1 to obtain the title compound as a freezing pale white crystal.

Yield: 0.67 g (31.9%)

Melting Point: 51–53° C.

EXAMPLE 6
Synthesis of 1-methoxy-4-allylthio-5,6,7,8-tetrahydrophthalazine 0.23 g(0.01 mol) of metallic sodium was dissolved in 30 ml of absolute methanol and then mixed with 0.93 ml(0.01 mol) of allylmercaptan. To this mixture was added 1.99 g(0.01 mol) of 1-methoxy-4-chloro-5,6,7,8-tetrahydrophthalazine obtained from Preparation 6. The reaction solution was refluxed for one hour and then treated according to the same manner as Example 1 to obtain the title compound as a freezing pale white crystal.

Yield: 1.37 g (58.1%)

Melting Point: 46–48° C.

EXAMPLE 7
Synthesis of 1-methoxy-4-allylthiophthalazine 0.23 g(0.01 mol) of metallic sodium was dissolved in 30 ml of absolute methanol and then mixed with 0.93 ml(0.01 mol) of allylmercaptan. To this mixture was added 1.95 g(0.01 mol) of 1-methoxy-4-chlorophthalazine obtained from Preparation 7. The reaction solution was refluxed for one hour and then treated according to the same manner as Example 1 to obtain the title compound as a freezing pale white crystal.

Yield: 1.58 g (68.1%)

Melting Point: 32–34° C.

NMR(CDCl$_3$, δ): 4.08(d, 2H, SCH$_2$), 4.20(s, 3H, OCH$_3$), 5.26(dd, 2H, CH$_2$), 6.10(m, 1H, CH), 7.82–8.17(m, 1H×4, aromatic)

EXAMPLE 8
Synthesis of 3-ethoxy-4-allylthiopyridazine 0.57 g(0.025 mol) of metallic sodium was dissolved in 40 ml of absolute methanol and then mixed with 2.49 ml(0.025 mol) of allylmercaptan. To this mixture was added 3.96 g(0.025 mol) of 3-ethoxy-6-chloropyridazine. The reaction solution was refluxed for 24 hours and then treated according to the same manner as Example 1 to obtain the title compound as a freezing pale white crystal.

Yield: 1.85 g (37.7%)

Melting Point: 28–30° C.

NMR(CDCl$_3$, δ): 1.35(t, 3H, CH$_3$), 4.45(q, 2H, OCH$_2$), 5.15(dd, 2H, CH$_2$), 5.95(m, 1H, CH), 6.70–7.15(dd, 1H×2, CH)

EXAMPLE 9
Synthesis of 3-ethoxy-4,5-dimethyl-6-allylthiopyridazine 0.23 g(0.01 mol) of metallic sodium was dissolved in 100 ml of absolute methanol and then mixed with 0.93 ml(0.01 mol) of allylmercaptan. To this mixture was added 1.87 g(0.01 mol) of 3-ethoxy-4,5-dimethyl-6-chloropyridazine obtained from Preparation 8. The reaction solution was refluxed for 3 hours and then treated according to the same manner as Example 1 to obtain the title compound as a freezing white crystal.

Yield: 0.15 g (6.7%)

Melting Point: 29–31° C.

EXAMPLE 10
Synthesis of 1-ethoxy-4-allylthio-5,6,7,8-tetrahydrophthalazine 0.23 g(0.01 mol) of metallic sodium was dissolved in 100 ml of absolute methanol and then mixed with 0.93 ml (0.01 mol) of allylmercaptan. To this mixture was added 2.13 g(0.01 mol) of 1-ethoxy-4-chloro-5,6,7,8-tetrahydrophthalazine obtained from Preparation 9. The reaction solution was refluxed for 3 hours and then treated according to the same manner as Example 1 to obtain the title compound as a freezing white crystal.

Yield: 0.36 g (14.4%)

Melting Point: 39–41° C.

EXAMPLE 11
Synthesis of 1-ethoxy-4-allylthiophthalazine 0.23 g(0.01 mol) of metallic sodium was dissolved in 100 ml of absolute methanol and then mixed with 0.93 ml(0.01 mol) of allylmercaptan. To this mixture was added 2.09 g(0.01 mol) of 1-ethoxy-4-chlorophthalazine obtained from Preparation 10. The reaction solution was refluxed for 3 hours and then treated according to the same manner as Example 1 to obtain the title compound as a freezing white crystal.

Yield: 0.79 g (32.1%)

Melting Point: 44–46° C.

EXAMPLE 12
Synthesis of 3-(n-propoxy)-6-allylthiopyridazine 1.15 g(0.05 mol) of metallic sodium was dissolved in 75 ml of absolute methanol and then mixed with 4.98 ml(0.05 mol) of allylmercaptan. To this mixture was added 8.63 g(0.05 mol) of 3-(n-propoxy)-6-chloropyridazine. The reaction solution was refluxed for 24 hours and then treated according to the same manner as Example 1 to obtain the title compound as a pale yellow oily residue.

Yield: 3.11 g (29.6%)

NMR(CDCl$_3$, δ): 1.10(t, 3H, CH$_3$), 1.82(q, 2H, CH$_2$), 3.95(d, 2H, SCH$_2$), 4.40(q, 2H, OCH$_2$), 5.25(dd, 2H, CH$_2$), 6.00(m, 1H, CH), 6.75–7.30(dd, 1H×2, CH)

EXAMPLE 13
Synthesis of 3-(2-propoxy)-6-allylthiopyridazine 2.30 g(0.1 mol) of metallic sodium was dissolved in 150 ml of absolute methanol and then mixed with 9.28 ml(0.1 mol) of allylmercaptan. To this mixture was added 17.26 g(0.1 mol) of 3-(2-propoxy)-6-chloropyridazine. The reaction solution was refluxed for 24 hours and then treated according to the same manner as Example 1 to obtain the title compound as a pale yellow oil.

Yield: 4.39 g (20.9%)

NMR(CDCl$_3$, δ): 1.35(d, 3H×2, CH(CH$_3$)$_2$), 3.90(d, 2H, SCH$_2$), 5.20(dd, 2H, CH$_2$), 5.45(m, 1H, OCH), 5.95(m, 1H, CH), 6.70–7.20(dd, 1H×2, CH)

EXAMPLE 14
Synthesis of 3-(n-butoxy)-6-allylthiopyridazine 1.15 g(0.05 mol) of metallic sodium was dissolved in 75 ml of absolute methanol and then mixed with 4.98 ml(0.05 mol) of allylmercaptan. To this mixture was added 9.33 g(0.05 mol) of 3-(n-butoxy)-6-chloropyridazine. The reaction solution was refluxed for 24 hours and then treated according to the same manner as Example 1 to obtain the title compound as a pale yellow oil.

Yield: 2.24 g (20.2%)

NNMR(CDCl$_3$, δ): 0.90(t, 3H, CH$_3$), 1.42(q, 2H, CH$_2$), 1.75(q, 2H, CH$_2$), 3.85(d, 2H, SCH$_2$), 4.40(t, 2H, OCH$_2$), 5.18(dd, 2H, CH$_2$), 6.00(m, 1H, CH), 6.70–7.20(dd, 1H×2, CH)

EXAMPLE 15
Synthesis of 3-(2-butoxy)-6-allylthiopyridazine 0.92 g(0.04 mol) of metallic sodium was dissolved in 120 ml of absolute methanol and then mixed with 3.98 ml(0.04 mol) of allylmercaptan. To this mixture was added 7.47 g(0.04 mol) of 3-(2-butoxy)-6-chloropyridazine. The reaction solution was refluxed for 24 hours and then treated according to the same manner as Example 1 to obtain the title compound as a pale yellow oil.

Yield: 1.19 g (13.3%)

NMR(CDCl$_3$, δ): 0.90(t, 3H, CH$_3$), 1.30(d, 3H, CH$_3$), 1.70(m, 2H, CH$_2$), 3.90(d, 2H, SCH$_2$), 5.15(dd, 2H, CH$_2$), 5.30(m, 1H, OCH$_2$), 5.98(m, 1H, CH), 6.70–7.15 (dd, 1H×2, CH)

EXAMPLE 16
Synthesis of 3-(t-butoxy)-6-allylthiopyridazine 0.46 g(0.02 mol) of metallic sodium was dissolved in 30 ml of absolute methanol and then mixed with 1.99 ml(0.02 mol) of allylmercaptan. To this mixture was added 3.75 g(0.02 mol) of 3-(t-butoxy)-6-chloropyridazine. The reaction solution was refluxed for 24 hours and then treated according to the same manner as Example 1 to obtain the title compound as a pale yellow oil.

Yield: 1.13 g (25.1%)

NMR(CDCl$_3$, δ): 1.60(s, 3H×3, C(CH$_3$)$_3$), 3.92(d, 2H, SCH$_2$), 5.20(dd, 2H, CH$_2$), 6.00(m, 1H, CH), 6.65–7.20(dd, 1H×2, CH)

EXAMPLE 17
Synthesis of 3-(n-pentyloxy)-6-allylthiopyridazine 1.15 g(0.05 mol) of metallic sodium was dissolved in 75 ml of absolute methanol and then mixed with 4.98 ml(0.05 mol) of allylmercaptan. To this mixture was added 10.03 g(0.05 mol) of 3-(n-pentyloxy)-6-chloropyridazine. The reaction solution was refluxed for 24 hours and then treated according to the same manner as Example 1 to obtain the title compound as a pale yellow needle crystal.

Yield: 4.21 g (35.3%)

Melting Point: 39–42° C.

NMR(CDCl$_3$, δ): 0.95(t, 3H, CH$_3$), 1.40(t, 2H×2, CH$_2$), 1.80(q, 2H, CH$_2$), 3.95(d, 2H, SCH$_2$), 4.45(m, 2H, OCH$_2$), 5.22(dd, 2H, CH$_2$), 6.00(m, 1H, CH), 6.75–7.30(m, 1H×2, CH)

EXAMPLE 18
Synthesis of 3-isopentyloxy-6-allylthiopyridazine 1.15 g(0.05 mol) of metallic sodium was dissolved in 150 ml of absolute methanol and then mixed with 4.98 ml(0.05 mol) of allylmercaptan. To this mixture was added 10.03 g(0.05 mol) of 3-isopentyloxy-6-chloropyridazine. The reaction solution was refluxed for 24 hours and then treated according to the same manner as Example 1 to obtain the title compound as a pale yellow oil.

Yield: 2.12 g (17.8%)

NMR(CDCl$_3$, δ): 0.92(d, 3H×2, CH(CH$_3$)$_2$), 1.70(m, 1H & 2H, CHCH$_2$), 3.90(d, 2H, SCH$_2$), 4.45(t, 2H, OCH$_2$), 5.15(dd, 2H, CH$_2$), 5.95(m, 1H, CH), 6.70–7.20(dd, 1H×2, CH)

EXAMPLE 19
Synthesis of 3-(2-N,N-dimethylaminoethoxy)-6-allylthiopyridazine 0.46 g(0.02 mol) of metallic sodium was dissolved in 30 ml of absolute 2-dimethylaminoethanol. To the resulting solution was added 3.73 g(0.02 mol) of 3-chloro-6-allylthiopyridazine. The reaction solution was stirred for 2 hours at room temperature and then treated according to the same manner as Example 1 to obtain the title compound as a yellow needle crystal.

Yield: 0.25 g (5.2%)

Melting Point: 36–38° C.

NMR(CDCl$_3$, δ): 1.88(d, 3H×2, N(CH$_3$)$_2$), 1.95(d, 2H×2, OCH$_2$CH$_2$), 4.00(d, 2H, SCH$_2$), 5.25(dd, 2H, CH$_2$), 6.10(m, 1H, CH), 6.85–7.20(m, 1H×2, CH)

EXAMPLE 20
Synthesis of 3-(2-hydroxyethoxy)-6-allylthiopyridazine 0.23 g(0.01 mol) of metallic sodium was dissolved in 30 ml of absolute methanol and then mixed with 1.00 ml(0.01 mol) of allylmercaptan. To this mixture was added 1.75 g(0.01 mol) of 3-(2-hydroxyethoxy)-6-chloropyridazine. The reaction solution was refluxed for 24 hours and then treated according to the same manner as Example 1 to obtain the title compound as a pale white needle crystal.

Yield: 1.24 g (58.5%)

Melting Point: 38–40° C.

NMR(CDCl$_3$, δ): 3.92(d, 2H, SCH$_2$), 4.10(s, 2H×2, OCH$_2$CH$_2$O), 5.22(dd, 2H, CH$_2$), 6.00(m, 1H, CH), 6.80–7.25(dd, 1H×2, CH)

EXAMPLE 21

Synthesis of 3-phenoxy-6-allylthiopyridazine 0.11 g(0.005 mol) of metallic sodium was dissolved in 30 g of dry phenol. To the resulting solution was added 0.93 g(0.005 mol) of 3-chloro-6-allylthiopyridazine and then the reaction solution was stirred for 3 hours at 160±5° C. After the reaction was allowed to stop, the reaction solution was cooled and adjusted to alkaline (pH 14) with 2N—NaOH, thereby precipitating the crystals. The precipitated crystal was extracted with diethyl ether and then treated according to the same manner as Example 1 to obtain the title compound as a crystal.

Yield: 0.42 g (34.5%)

Melting Point: 71–73° C.

NMR(CDCl$_3$, δ): 3.95(d, 2H, SCH$_2$), 5.22(dd, 2H, CH$_2$), 6.00(m, 1H, CH), 680–7.10(m, 1H×2, CH), 7.15–7.45 (m, 1H×5, aromatic)

EXAMPLE 22

Synthesis of 3-benzyloxy-6-allylthiopyridazine 0.11 g(0.005 mol) of metallic sodium was dissolved in 20 ml of dry benzylalcohol. To the resulting solution was added 0.93 g(0.005 mol) of 3-chloro-6-allylthiopyridazine and then the reaction solution was stirred for 2 hours at 80±5° C. To remove the excessive benzylalcohol and the insoluble material (NaCl), the reaction mixture was purified with silica gel column chromatography (eluent: n-hexane/ethyl acetate=40/1, v/v) to obtain the title compound as a needle crystal.

Yield: 0.92 g (71.3%)

Melting Point: 56–58° C.

Recrystallizing solvent: ethanol

NMR(CDCl$_3$, δ): 4.00(d, 2H, SCH$_2$), 5.25(dd, 2H, CH$_2$), 5.55(s, 2H, OCH$_2$), 6.05(m, 1H, CH), 6.85–7.30(dd, 1H×2, CH), 7.35–7.65(m, 1H×5, aromatic)

EXAMPLE 23

Synthesis of 3-(4-methylphenoxy)-6-allylthiopyridazine 0.23 g(0.01 mol) of metallic sodium was dissolved in 30 ml of dry p-cresol. To the resulting solution was added 1.87 g(0.01 mol) of 3-chloro-6-allylthiopyridazine and then the reaction solution was stirred for 5 hours at 100±5° C. After the reaction was allowed to stop, the reaction solution was cooled and adjusted to alkaline (pH 14) with 150 ml of 2N—NaOH, thereby precipitating the crystals. The precipitated crystal was extracted with diethyl ether, washed twice with purified water, dried over anhydrous magnesium sulfate and then concentrated to remove diethyl ether. The resulting oily residue was slowly cooled to obtain the title compound as a pale white amorphous crystal.

Yield: 1.07 g (41.5%)

Melting Point: 115–117° C.

NMR(CDCl$_3$, δ): 2.35(s, 3H, CH$_3$), 3.95(d, 2H, SCH$_2$), 5.20(dd, 2H, CH$_2$), 6.00(m, 1H, CH), 6.98–7.10(dd, 1H×2, CH), 7.18–7.35(m, 1H ×4, aromatic)

EXAMPLE 24

Synthesis of 3-(3-methylphenoxy)-6-allylthiopyridazine 0.23 g(0.01 mol) of metallic sodium was dissolved in 30 ml of dry m-cresol. To the resulting solution was added 1.87 g(0.01 mol) of 3-chloro-6-allylthiopyridazine. The reaction solution was stirred for 5 hours at 100±5° C. and then treated according to the same manner as Example 23 to obtain the title compound as a pale white needle crystal.

Yield: 0.94 g (36.4%)

Melting Point: 48–50° C.

NMR(CDCl$_3$, δ): 2.30(s, 3H, CH$_3$), 3.90(d, 2H, SCH$_2$), 5.15(dd, 2H, CH$_2$), 5.95(m, 1H, CH), 6.95(m, 1H×2, CH), 7.22(m, 1H×4, aromatic)

EXAMPLE 25

Synthesis of 3-(2-methylphenoxy)-6-allylthiopyridazine 0.23 g(0.01 mol) of metallic sodium was dissolved in 30 ml of dry o-cresol. To the resulting solution was added 1.87 g(0.01 mol) of 3-chloro-6-allylthiopyridazine. The reaction solution was stirred for 5 hours at 100±5° C. and then treated according to the same manner as Example 23 to obtain the title compound as a pale white needle crystal.

Yield: 0.48 g (18.6%)

Melting Point: 78–80° C.

NMR(CDCl$_3$, δ): 2.20(s, 3H, CH$_3$), 3.92(d, 2H, SCH$_2$), 5.20(dd, 2H, CH$_2$), 6.00(m, 1H, CH), 7.00–7.35(m, 1H×2 & 1H×4, CH & aromatic)

EXAMPLE 26

Synthesis of 3-phenyl-6-allylthiopyridazine 0.23 g(0.01 mol) of metallic sodium was dissolved in 30 ml of absolute methanol and then mixed with 0.93 ml(0.01 mol) of allylmercaptan. To this mixture was added 1.90 g(0.01 mol) of 6-chloro-3-phenylpyridazine. The reaction solution was refluxed for 5 hours and concentrated under reduced pressure to remove methanol. 100 ml of diethyl ethers was added to the residue and vigorously stirred for 10 minutes. The materials insoluble in diethyl ether was removed and the remaining solution was washed twice with 50 ml of purified water, dried over anhydrous magnesium sulfate and then concentrated under reduced pressure to remove diethyl ether. In this manner, the title compound was obtained as a white crystal.

Yield: 2.18 g (95.6%)

Melting Point: 96–98° C.

NMR(CDCl$_3$, δ): 4.08(d, 2H, SCH$_2$), 5.28(dd, 2H, CH$_2$), 6.08(m, 1H, CH), 7.48(m, 1H×2, CH)

Experiment 1

Acute toxicity test

The acute toxicity test was carried out to quantitatively and qualitatively examine the toxicity which occurs within a short period of time after a single administration of the test compound to the experimental animal.

In this experiment, the acute toxicity test was conducted using 5–6 weeks ICR male mouse obtained from Korea Experimental Animal Center. From 6 p.m., the day before administration of the test compound, to 9 a.m. the day on which the test compound is administered, mouse was fasted. The test compound was ground and suspended in corn oil and then administered in the dose of 1000 to 6000 mg/kg to the experimental animal. For each dose, 6 animals were used. The test compound was prepared and used on that day, and was single administered via oral route by means of a needle. After the compound of Example 4, as typical example of the compound according to the present invention was administered, the survived and died animals were observed during 14 days. The result thereof is shown in the following Table 1. According to the analysis of this result by Litchfield-Wilcoxon method, LD$_{50}$ value of the compound is shown to be 3.95 g/kg (95% confidence interval: 3.26–4.78 g/kg).

TABLE 1

| Dose(mg/kg) | 1000 | 2000 | 3000 | 4000 | 5000 | 6000 |
|---|---|---|---|---|---|---|
| D/T | 0/6 | 0/6 | 1/6 | 3/6 | 4/6 | 6/6 |

Note: D/T = Number of died animals / Number of test animals

Experiment 2

Effect of the compound according to the present invention on the expression rate of mEH and GST To confirm the effect of allylthiopyridazine derivative according to the present invention on the expression rate of mEH and GST, the respective compound was orally administered for 5–6 weeks to SD male rat in the dose of 100 mg/kg. After 24 hours from administration, the amount of mRNAs for mEH and GSTA2 produced in liver tissue was quantified according to Northern Blot analysis. The results obtained are shown in FIGS. 1 and 2 in terms of the relative increasing multiple in comparison to the non-treatment group. From FIGS. 1 and 2, it can be noted that all the test compounds show twice or more increase in the expression rate, and several compounds show an exceptional increase in the expression rate.

Experiment 3

Effect of inhibiting hepatic disorder induced by carbon tetrachloride

The liver protective effect of the compound according to the present invention was examined according to the known method [see, Philippe letteron et al., *Biochemical Pharmacology*, 39, 12, 2027–2034, 1990] as specifically described below.

The compound according to the present invention was suspended in corn oil and the resulting suspension was administered in an amount of 1.0 ml/kg. Each group was composed of 3 to 10 male ICR mice (5–6 weeks) and the test compound was orally administered for 3 days in the dose of 50 mg/kg per day. After the test compound was administered, carbon tetrachloride was intraperitoneally injected in an amount of 100 $\mu$l/kg. In this experiment, silymarin was used as the comparative compound. After 24 hours from administration of carbon tetrachloride, blood was taken from the test animal by cardiac perforation and ALT value in serum was determined. The result obtained is described in the following Table 2 (in which ALT value is represented by mean±SE). The ALT unit in serum was determined by centrifuging blood to separate serum as the supernatant, and then the separated serum were subjected to Reitman-Frankel method by means of a commercially available kit (BC101-O,P, Youngdong Pharm.). That is, DL-alanine and $\alpha$-ketoglutarate were used as the substrate solution to which 2,4-dinitrophenylhydrazine was added to produce hydrazone. Then, sodium hydroxide was added to hydrazone to colorize and then the absorbance was measured at 505 nm.

In addition, liver was removed from the test animals, stained (×100) with hematoxylin and eosin and then observed by microscope. The degree of hepatocyte necrosis was evaluated according to the following 5 grades: 0 no lesion, 1 mild lesion, 2 moderate lesion, 3 severe lesion and 4 diffused lesion. The result as obtained is described in the following Table 3. According to the statistic analysis of the results described in Tables 2 and 3, it could be seen that only the non-treated group and the group treated with the compound of Example 4 significantly differ from the $CCl_4$ treated group (p<0.01).

TABLE 2

| | Number of test animals | Serum ALT value (KA unit/l) | Inhibiting rate (%) |
|---|---|---|---|
| Non-treated group | 3 | 157 ± 48 | 100 |
| $CCl_4$ treated group | 9 | 9086 ± 1017 | 0 |
| Compound of Example 12 + $CCl_4$ treated group | 9 | 5585 ± 705 | 40 |
| Compound of Example 8 + $CCl_4$ treated group | 7 | 6123 ± 2230 | 33 |
| Compound of Example 4 + $CCl_4$ treated group | 10 | 3966 ± 1116 | 57 |
| Silymarin + $CCl_4$ treated group | 10 | 7602 ± 662 | 17 |

TABLE 3

| | Number of test animals | Degree of necrosis | | | | |
|---|---|---|---|---|---|---|
| | | 0 | 1 | 2 | 3 | 4 |
| Non-treated group | 3 | 3 | 0 | 0 | 0 | 0 |
| $CCl_4$ treated group | 9 | 0 | 0 | 0 | 0 | 9 |
| Compound of Example 12 + $CCl_4$ treated group | 9 | 0 | 0 | 2 | 3 | 4 |
| Compound of Example 8 + $CCl_4$ treated group | 7 | 0 | 1 | 2 | 1 | 3 |
| Compound of Example 4 + $CCl_4$ treated group | 10 | 0 | 1 | 5 | 2 | 2 |
| Silymarin + $CCl_4$ treated group | 10 | 0 | 0 | 1 | 7 | 2 |

Experiment 4

Effect of inhibiting hepatic disorder induced by acetaminophen (APAP)

The liver protective effect of the compound according to the present invention was examined according to the known method [see, Wang et al., *Toxicology and applied Pharmacology*, 136, 146–154, 1996] as specifically described below.

The compound according to the present invention was suspended in corn oil and the resulting suspension was administered in an amount of 1.0 ml/kg. Each group was composed of 3 to 10 male ICR mice (5–6 weeks) and the test compound was orally administered for 3 days in the dose of 50 mg/kg per day. After 2 hours from the last administration of the test compound, acetaminophen was orally administered in an amount of 0.5 g/kg. In this experiment, silymarin was used as the comparative compound. After 22 hours from the administration of acetaminphen, blood was taken from the individual test animal and ALT and LDH values in serum were determined. The results as obtained are described in the following Tables 4 and 5 (in which ALT and LDH values are represented by mean±SE). In addition, liver was removed from the test animals and then observed according to the same manner as Experiment 3 to evaluate the degree of hepatocyte necrosis. The result as obtained is described in the following Table 6. According to the statistic analysis of the results described in Tables 4 to 6, it could be seen that only the non-treated group and the groups treated with the compounds of Examples 4 and 8 significantly differ from the APAP treated group (p<0.01).

TABLE 4

| | Number of test animals | Serum ALT value (KA unit/l) | Inhibiting rate (%) |
|---|---|---|---|
| Non-treated group | 3 | 64 ± 3 | 100 |
| APAP treated group | 10 | 3666 ± 825 | 0 |
| Compound of Example 12 + APAP treated group | 10 | 2749 ± 1352 | 25 |
| Compound of Example 8 + APAP treated group | 9 | 98 ± 26 | 99 |
| Compound of Example 4 + APAP treated group | 10 | 186 ± 118 | 97 |
| Silymarin + APAP treated group | 10 | 2562 ± 712 | 31 |

TABLE 5

| | Number of test animals | Serum LDH value (KA unit/l) | Inhibiting rate (%) |
|---|---|---|---|
| Non-treated group | 3 | 680 ± 46 | 100 |
| APAP treated group | 10 | 12375 ± 2598 | 0 |
| Compound of Example 12 + APAP treated group | 10 | 5480 ± 2346 | 59 |
| Compound of Example 8 + APAP treated group | 9 | 1193 ± 546 | 95.6 |
| Compound of Example 4 + APAP treated group | 10 | 703 ± 83 | 99.8 |
| Silymarin + APAP treated group | 10 | 8095 ± 3534 | 37 |

TABLE 6

| | Number of test animals | Degree of necrosis | | | | |
|---|---|---|---|---|---|---|
| | | 0 | 1 | 2 | 3 | 4 |
| Non-treated group | 6 | 6 | 0 | 0 | 0 | 0 |
| APAP treated group | 5 | 0 | 0 | 0 | 0 | 5 |
| Compound of Example 12 + APAP treated group | 6 | 0 | 1 | 1 | 1 | 3 |
| Compound of Example 8 + APAP treated group | 9 | 7 | 0 | 2 | 0 | 0 |
| Compound of Example 4 + APAP treated group | 10 | 5 | 4 | 1 | 0 | 0 |
| Silymarin + APAP treated group | 10 | 0 | 0 | 2 | 3 | 5 |

Experiment 5
Protective effect against radiation damage

In order to confirm the protective effect of the compound of the present invention against radiation damage, the following test was conducted.

Figure 3:
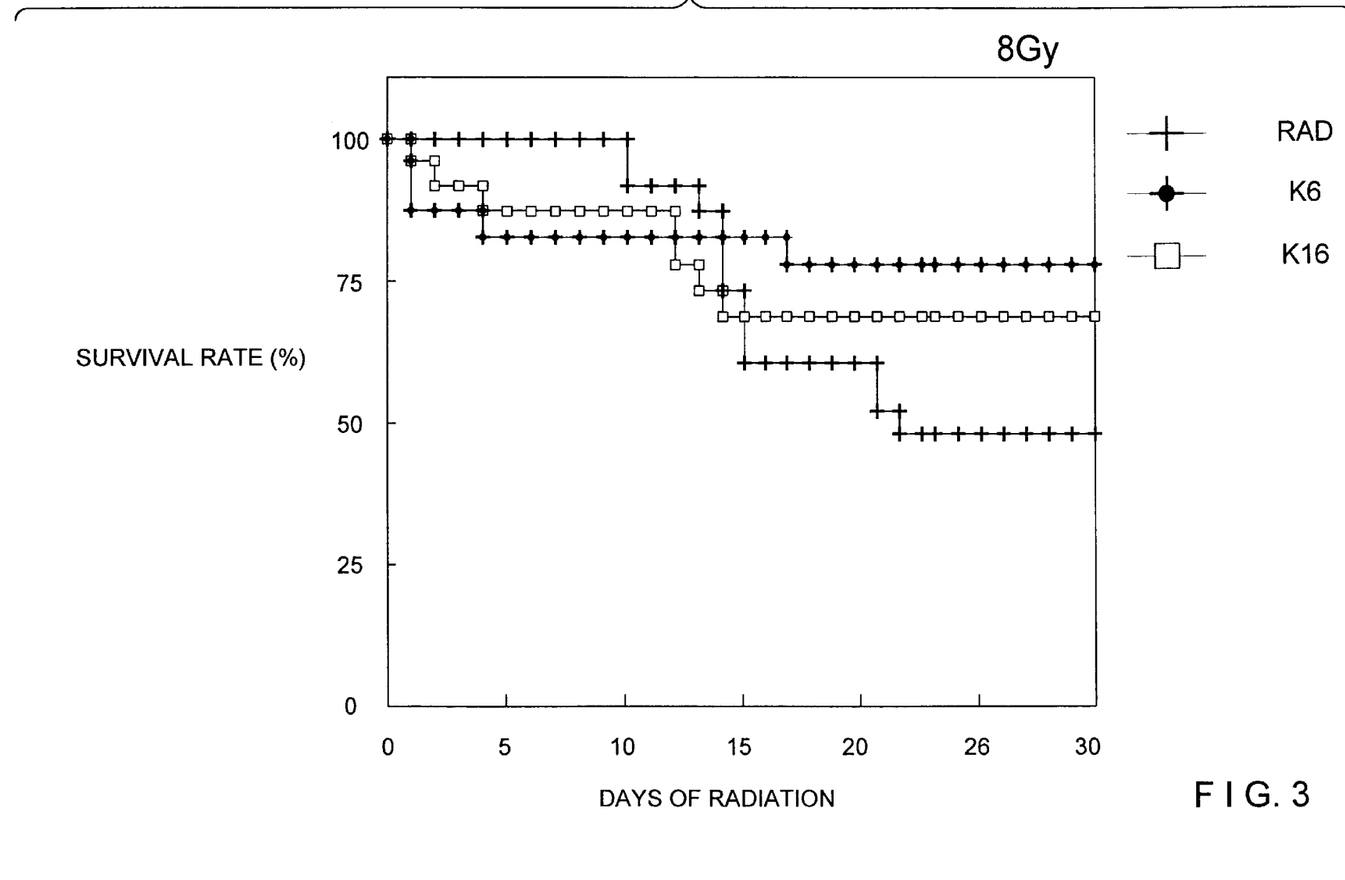
FIG. 3 shows the survival rate of mouse during 30 days of 8 Gy radiation, after being administered with the compound according to the present invention.

Male ICR mouse was bred in a chamber to which sterile atmosphere is supplied, at inner temperature 20–23° C. and relative humidity 50% with sufficient water and feed. When the weight of mouse reached 20–25 g, the compound of the present invention was suspended in corn oil and then administered for 2 days in the dose of 100 mg/kg (1 ml/kg) per day. After 3 hours from the last administration of the test compound, 8 or 9 Gy radiation was irradiated to mouse. Specifically, mouse was introduced into a box made of acryl which limited his movement, and then radiation produced from $^{60}Co$ radioactive material was irradiated to whole body at the irradiating rate of 115.8 cGy/min. The dimension of acryl box was 31×31 $cm^2$, which is the same as the irradiating area of radiation. After 7 days of irradiation of γ-ray, mouse was sacrificed to conduct the histopathologic observation. The result of examining the survival rate during 30 days of irradiation of 8 Gy radiation is shown in FIG. 3, and the result of determining the survival rate after a certain period (10, 13 or 30 days) from irradiation of 8 or 9 Gy radiation is described in the following Table 7.

TABLE 7

| | Radiation | Compound of Example 4 + radiation | Compound of Example 8 + radiation |
|---|---|---|---|
| 30 days of 8 Gy radiation | | | |
| survival number | 11/23 | 18/23 | 16/23 |
| survival rate (%) | 48 | 78 | 70 |
| 10 days of 9 Gy radiation | | | |
| survival number | 7/23 | 16/23 | 17/23 |
| survival rate (%) | 30 | 70 | 74 |
| 13 days of 9 Gy radiation | | | |
| survival number | 0/23 | 3/23 | 5/23 |
| survival rate (%) | 0 | 13 | 22 |

What is claimed is:

1. An allylthiopyridazine compound represented by formula (I):

(I)

or a pharmaceutically acceptable salt thereof, in which $R_1$ represents halogen atom, lower alkoxy, dialkylaminoalkoxy, hydroxyalkoxy, phenoxy substituted or unsubstituted with lower alkyl, benzyloxy, or phenyl and $R_2$ and $R_3$ independently of one another represent hydrogen or lower alkyl, or $R_2$ and $R_3$ together with carbon atom to which they are attached form a tetrahydrophthalazine ring provided that $R_2$ and $R_3$ are other than hydrogen when $R_1$ is chloro.

2. A compound as defined in claim 1 wherein $R_1$ represents chloro, methoxy, ethoxy, n-propoxy, 2-propoxy, n-butoxy, 2-butoxy, t-butoxy, n-pentyloxy, i-pentyloxy, 2-(N,N-dimethylamino)ethoxy, 2-hydroxyethoxy, phenoxy, benzyloxy, 4-methylphenoxy, 3-methylphenoxy, 2-methylphenoxy or phenyl, and $R_2$ and $R_3$ independently of one another represent hydrogen or methyl, or $R_2$ and $R_3$ together with carbon atom to which they are attached form a tetrahydrophthalazine ring.

3. A process for preparing a compound of formula (I):

(I)

in which $R_1$ represents halogen atom, lower alkoxy, dialkylaminoalkoxy, hydroxyalkoxy, phenoxy substituted or unsubstituted with lower alkyl, benzyloxy, or phenyl and $R_2$ and $R_3$ independently of one another represent hydrogen or lower alkyl, or R₂ and R₃ together with carbon atom to which they are attached form a tetrahydrophthalazine ring, provided that R₂ and R₃ are other than hydrogen when R₁ is chloro, comprising reacting a compound of formula (II):

(II)

wherein R₁, R₂ and R₃ are defined as above and X represents a halogen atom, with a compound of formula (III):

(III)

in a solvent in the presence of a base to produce the compound of formula (I):

(I)

4. A process for preparing the compound of formula (I):

(Ia)

in which R₁' represents lower alkyl, dialkylaminoalkyl, hydroxyalkyl, phenyl substituted or unsubstituted with lower alkyl, or benzyl, comprising reacting a compound of formula (IV):

(IV)

wherein X represents a halogen atom with a compound of formula (V):

(V)

wherein R₁' represents lower alkyl, dialkylaminoalkyl, hydroxyalkyl, phenyl substituted or unsubstituted with lower alkyl, or benzyl, in a solvent to produce a compound of formula (Ia):

(Ia)

wherein R₁' is defined as above.

5. The process as defined in claim 3 wherein the solvent is selected from methanol, ethanol, acetone, methylethyl ketone or a mixture thereof.

6. The process as defined in claim 3 wherein the base comprises one or more metals selected from the group consisting of sodium, potassium and lithium.

7. The process as defined in claim 4 wherein the solvent is selected from methanol, ethanol, acetone, methylethyl ketone or a mixture thereof.

8. The process as defined in claim 4 where in the compound of formula (V) is prepared by reacting sodium metal with a compound of formula R₁'OH wherein R₁' is as defined in claim 4.

9. A pharmaceutical composition for prevention or treatment of hepatic disease or for protecting human tissues from radiation which comprises an effective amount of the compound of formula (I) as defined in claim 1 together with a pharmaceutically acceptable carrier.

10. The composition as defined in claim 9 wherein the pharmaceutically acceptable carrier is selected from starch, lactose, cellulose derivatives, sugar or a mixture thereof.

11. A method for treating or preventing hepatic diseases which comprises administering an effective amount of a compound of formula (I) as defined in claim 1 to a patient in need thereof.

12. A process for protecting human tissues from radiation which comprises administering an effective amount of a compound of formula (I) as defined in claim 1 to a patient in need thereof.

* * * * *